United States Patent [19]

Caetano-Anolles et al.

[11] Patent Number: 5,492,810

[45] Date of Patent: Feb. 20, 1996

[54] DNA SILVER STAINING

[75] Inventors: Gustavo Caetano-Anolles; Brant J. Bassam; Peter M. Gresshoff, all of Knoxville, Tenn.

[73] Assignee: University of Tennessee Research Corporation, Knoxville, Tenn.

[21] Appl. No.: 193,514

[22] Filed: Feb. 8, 1994

Related U.S. Application Data

[63] Continuation of Ser. No. 676,869, Mar. 28, 1991, abandoned.

[51] Int. Cl.⁶ .............................. C12Q 1/68; G01N 27/26
[52] U.S. Cl. .................... 435/6; 204/456; 204/462
[58] Field of Search .................... 435/6, 86; 436/94; 204/182.8

[56] References Cited

U.S. PATENT DOCUMENTS

| | | | |
|---|---|---|---|
| 4,405,720 | 9/1983 | Merril | 436/86 |
| 4,416,998 | 11/1983 | Adams et al. | 436/86 |
| 4,468,466 | 8/1984 | Morrissey | 436/86 |
| 4,555,490 | 11/1985 | Merril | 436/86 |
| 4,575,452 | 3/1986 | Lee et al. | 422/61 |
| 4,582,808 | 4/1986 | Oosawa et al. | 436/86 |
| 4,703,016 | 10/1987 | Merril | 436/86 |

OTHER PUBLICATIONS

Blum etal. Electrophoresis 8:93–99, 1987.
Bassam et al. Analytical Biochem. 196:80–83, 1991.
Lomholt et al. Analytical Biochem. 164:146–149, 1987.
Allen et al. Biotechniques 7:736–741.

*Primary Examiner*—Margaret Parr
*Assistant Examiner*—Eggerton Campbell
*Attorney, Agent, or Firm*—Weiser & Associates

[57] ABSTRACT

A method for visualizing nucleic acids in a polyacrylamide gel. The method comprises fixing the nucleic acids with 10% acetic acid for about 20 minutes, washing the gel multiple times with water for about 2 minutes, impregnating the gel with silver nitrate at a concentration of about 1.0 g/l and about 1.5 ml/l of 37% formaldehyde for about 30 minutes, developing the gel with sodium carbonate at a concentration of about 30 g/l, 1.5 ml/l of 37% formaldehyde and sodium thiosulfate pentahydrate at a concentration of about 2.0 mg/l for between about 2 minutes and about 5 minutes, and then stopping the development of the gel by treatment with 10% acetic acid for about 5 minutes.

11 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 8 bases
        ( B ) TYPE: nucleic acid
        ( C ) STRANDEDNESS: single
        ( D ) TOPOLOGY: linear ( i i ) MOLECULE TYPE: DNA PRIMER ( i i i ) HYPOTHETICAL: no ( x i ) SEQUENCE DESCRIPTION: SEQ ID NO:1:

A A T G C A G C    8

( 2 ) INFORMATION FOR SEQ ID NO:2:

( i ) SEQUENCE CHARACTERISTICS:
        ( A ) LENGTH: 8 bases
        ( B ) TYPE: nucleic acid
        ( C ) STRANDEDNESS: single
        ( D ) TOPOLOGY: linear ( i i ) MOLECULE TYPE: DNA Primer ( i i i ) HYPOTHETICAL: No ( x i ) SEQUENCE DESCRIPTION: SEQ ID NO:2:

C G C G G C C A    8

DNA SILVER STAINING

This application is a continuation of application Ser. No. 07/676,869, filed Mar. 28, 1991, abandoned.

BACKGROUND OF THE INVENTION

1. Field of the Invention

The present invention relates to methods for visualizing biological materials in gels. More specifically, it relates to the visualization of nucleic acids in polyacrylamide gels.

2. Description of the Related Art

Modern biotechnological techniques require the visualization of very small amounts of biological materials, especially nucleic acids. For example, restriction length fragment polymorphism (RFLP) mapping is a procedure which first divides a length of DNA into hundreds (or thousands) of much smaller fragments. The collection of fragments is then separated by length using electrophoresis. This results in a particular pattern of fragment bands. In general, the bands are not visualized directly but are usually treated with a probe such that at least some of the bands may be seen.

Present techniques for visualization use either hybridization probes or direct visualization. In hybridization techniques, a probe (a radioactive isotope or a fluorescent moiety) is attached or incorporated into a short segment of nucleic acid. The short segment binds to (hybridizes with) any strand of nucleic acid which contains a complementary segment of nucleic acid. Hybridization techniques are useful where the identification of the presence and location of a particular sequence of nucleic acids is desired. Usually, only a few of the hundreds of bands will be visualized by the probe. Hybridization techniques are specific and usually quite sensitive. Probes using radioactive isotopes as labels are detectable at about 1 pg/mm$^2$ band cross-section. Since the probe is so specific, there is very little background interference, which contributes significantly to the sensitivity of the technique. However, the use of radioisotopes as probes pose a significant threat to the health of workers and to the environment.

In contrast, the direct visualization techniques usually mark all of the bands in the gel and not just a specific few. In addition, there is some deposition of the visualizing material, such as silver, into the background gel. By far, silver staining is the preferred method of direct visualization of nucleic acids in gels. The methods for silver staining are derived either from histological procedures using ammoniacal silver solutions or from photochemical procedures in which silver ions bind to the nucleic acid bases and are then selectively reduced by chemical agents or light.

Generally, silver staining methods are not as sensitive as the radioisotopic methods since the gel will usually take up some of the silver ions giving a lowered contrast between the gel background and the bands of nucleic acids. Some prior silver staining methods have been made as sensitive as radioisotope methods but they are complex, time consuming and require the preparation of several moderately unstable solutions immediately prior to use. These complications greatly decrease the usability of the most sensitive silver staining methods.

Accordingly, it is an object of the present invention to provide a method for visualizing nucleic acids in polyacrylamide gels that has substantially the same sensitivity and ease of use as radioisotope markers without the inherent radiation risks to technicians or the environment.

Additionally, it is an object of the present invention to provide a method for visualizing nucleic acids in polyacrylamide gels using a silver staining technique that is neither as complex nor as time consuming as methods in the prior art while having the sensitivity of those methods using radioisotopes.

SUMMARY OF THE INVENTION

A method of silver staining has been discovered which gives the ease and sensitivity of radioisotope methods. Further, this method provides the safety of previous silver staining methods without the complexities. The method is unexpectedly sensitive when compared to prior staining methods providing at least one order of magnitude improvement in sensitivity.

The present invention provides a method for visualizing nucleic acids in a polyacrylamide gel. The method includes the steps of fixing the nucleic acids while in the gel with acetic acid for a period of between about 10 minutes and about 30 minutes. The acetic acid has a concentration of between about 5% and about 15% in water. In a preferred embodiment, the nucleic acids are fixed by treatment with 10% acetic acid for about 20 minutes.

Following fixing, the gel containing the fixed nucleic acids is washed, preferably at least three times, with water. In the preferred procedure each of the multiple washings is carried out for a period of between about 1 minute and about 3 minutes. The gel, with the contained nucleic acids, is washed three times for 2 minutes each in the most preferred embodiment.

The washed gel with the contained nucleic acids is next impregnated by treating the nucleic acids with a mixture of silver nitrate and between about 1.0 ml/l and about 2.0 ml/l of 37% formaldehyde for between about 20 minutes and about 40 minutes. The treatment uses silver nitrate at a concentration of between about 0.5 g/l and about 1.5 g/l. In the preferred embodiment of the invention, this treatment of the nucleic acids is carried out with a solution containing silver nitrate, at a concentration of about 1.0 g/l, and 1.5 ml/l of 37% formaldehyde for about 30 minutes.

After impregnation, the gel with the contained nucleic acids is developed by treatment with a mixture containing sodium carbonate (at between about 20 g/l and about 40 g/l), between about 1.0 ml/l and about 2.0 ml/l of 37% formaldehyde, and sodium thiosulfate pentahydrate (at between about 2.0 mg/l and about 3.0 mg/l) for between about 2 minutes and about 5 minutes. A preferred impregnation step involves the treatment of the gel and nucleic acids with a mixture of sodium carbonate, at about 30 g/l, about 1.5 ml/l of 37% formaldehyde, and sodium thiosulfate pentahydrate, at about 2.0 mg/l, for between about 2 minutes and about 5 minutes.

The development of the gel is stopped by treatment with acetic acid, at a concentration of between about 5% and about 15%, for between about 3 minutes and 7 minutes. When 10% acetic acid is used, the treatment is for about 5 minutes.

The bands of nucleic acid become visible on the gel during the development step. Once the complete treatment is finished, nucleic acids are detectable to at least as little as 1 pg/mm$^2$ band cross-section. This represents a level of resolution that is comparable to that available with radioisotope markers and is at least one order of magnitude superior to previous silver staining methods. In addition, this resolution is available with solutions that may be prepared well beforehand and stored for immediate or later use.

The gel may be unsupported or it may have a polyester backing film (such as GELBOND PAG polyester from FMC) to support the gel. Gels cast on such films are easily handled during staining and, when dried, produce a permanent record. However, the polyester film layer has the disadvantage of decreasing the surface area of the gel in contact with the staining solutions resulting in a slowing of the diffusion of solutes into and out of the gel matrix. This not only lengthens the time of image development during staining but also increases the amount of background staining. To overcome this problem, the treatments are conducted at temperatures between about 8° C. and about 12° C. It is believed that lower temperatures compensate for diminished ion diffusion in polyester backed gels by slowing the reduction of the silver ions with formaldehyde. The resolution of bands of nucleic acids on backed gels is comparable to the resolution on unsupported gels.

It was surprising to discover that the limit of detection upon visual inspection of nucleic acids of the present invention is approximately 1 pg/mm$^2$ band cross-section. The most sensitive nucleic acid staining previously reported is 5 to 10 times less sensitive [J. L. Beidler, P. R. Hilliard and R. L. Hill, *Anal. Biochem.*, Vol. 126, pp. 374–380 (1982)]. The method of the present invention also surpasses all other reported silver-staining protocols by at least one order of magnitude in sensitivity [10 pg/mm$^2$ reported in R. C. Allen, G. Graves and B. Budowle, *Biotechniques*, Vol. 7, pp. 736–744 (1989); 20 pg/mm$^2$ reported in H. Blum, H. Beier and H. J. Gross, *Electrophoresis*, Vol. 8, pp. 93–99 (1987); 30 pg/mm$^2$ reported in D. Goldman and C. R. Merril, *Electrophoresis*, Vol. 3, pp. 24–26 (1982)].

BRIEF DESCRIPTION OF THE DRAWING

In order to provide a better understanding of the present invention, the following example is given by way of illustration and not be way of limitation. The present Example may be better understood by reference to FIG. 1 which is a comparison of silver staining techniques. Lanes 1–3 were stained using the method of the present invention and lanes 4–6 were stained using the standard method of C. R. Merril, D. Goldman, S. A. Sedman and M. H. Ebert, *Science*, Vol. 211, pp. 1437–1438 (1981).

DESCRIPTION OF THE PREFERRED EMBODIMENTS

EXAMPLE I

Figure 1:
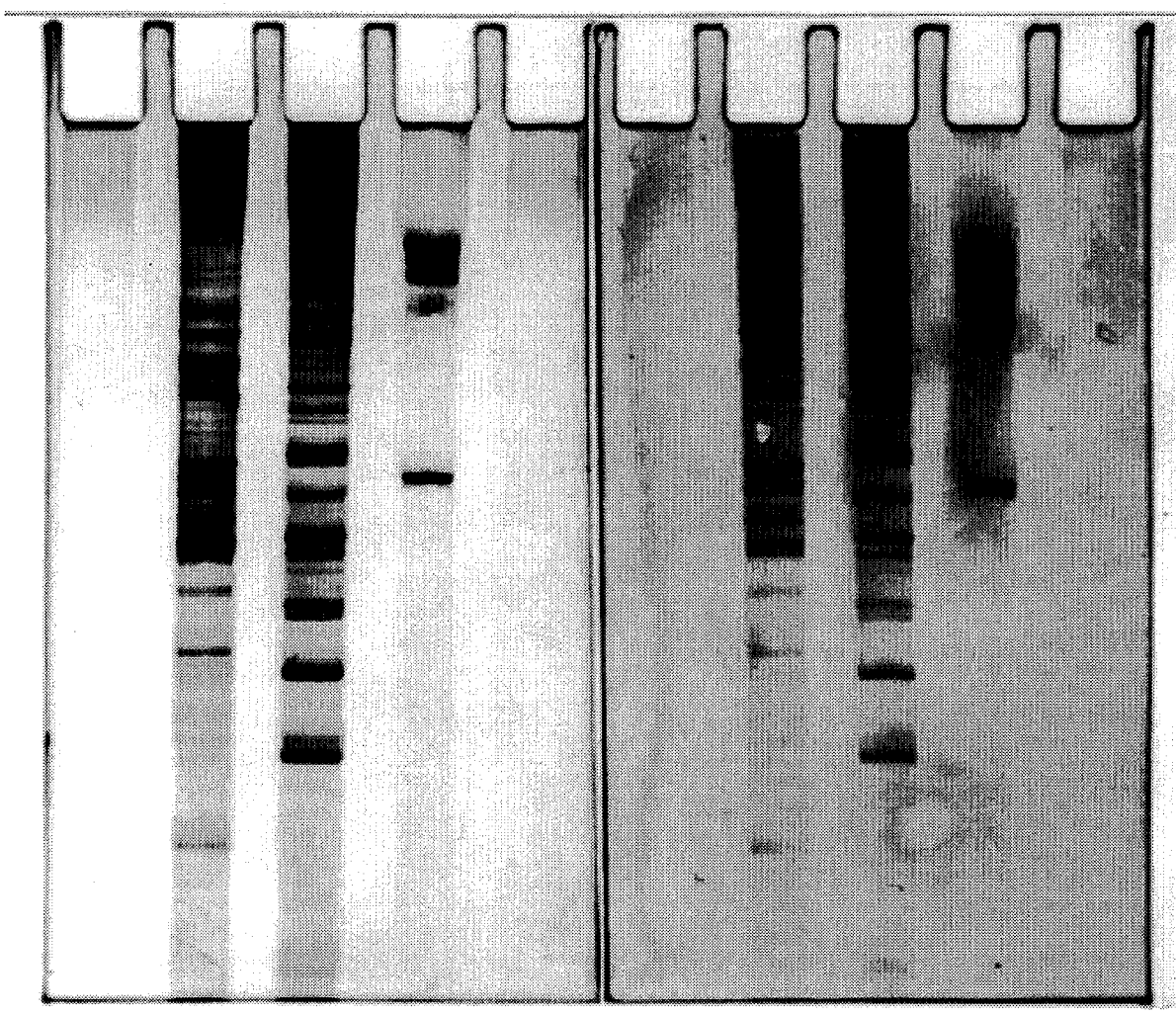

All chemicals used for the preparation of buffers and gels were electrophoresis grade from Bio-Rad Laboratories. Phage φX174 Hae III restriction digest was purchased from Bethesda Research, and pBR322 DNA BstN I digest was purchased from New England Biolabs. Ethanol was chemically pure. Formaldehyde and nitric acid were obtained from Mallinckrodt, Inc., sodium thiosulfate pentahydrate was obtained from Sigma Chemical Co., silver nitrate was obtained from EM Science, and sodium carbonate was obtained from Eastman-Kodak. All solutions were prepared in deionized water (>10MΩ-cm).

Polyacrylamide gels were prepared as 0.45 mm thick slabs with 5% polyacrylamide and 1.6M or 7M urea. The gel slabs were placed in a MINI-PROTEAN II cell from Bio-Rad. The ratio of acrylamide to the crosslinker piperazine diacrylamide (Bio-Rad) was 20:1. Gels were run with or without polyester backing (GELBOND PAG polyester backing film from FMC) to support the gel. The gels and electrophoresis running buffer contained 100 mM Tris.HCl, 83 mM boric acid, and 1 mM Na$_2$EDTA.H$_2$O at pH 8.3. Nucleic acid samples were applied to the gels in 5 μl aliquots containing 5M urea and 0.0008% xylene cyanol FF dye. Electrophoresis was conducted at 70 V until the dye front reached the end of the gel.

Segments of genomic DNA were amplified using a single oligonucleotide as is described in G. Caetano-Anollés, B. J. Bassam and P.M. Gresshoff, *Biotechnology*, in press (1991). Briefly, 10–20 pg of genomic template DNA was amplified in a total volume of 100 μl containing 1 μl of an 8 nucleotide primer and 2.5 units of AMPLITAQ polymerase (Perkin Elmer/Cetus) in a reaction buffer (10 mM Tris.HCl at pH 8.3, 50 mM KCl, and 2.5 mM MgCl$_2$) containing 200 μM each of dATP, dCTP, dGTP and dTTP (Pharmacia) for 35 cycles in a thermocycler (Ericomp) (1 second at 96° C., 10 seconds at 30° C., and 10 seconds at 72° C. for each cycle).

Segments of the genomic DNA of the bacterium *Candida albicans* were amplified, as above, using either primer sequence SEQ ID No: 1 AATGCAGC or SEQ ID No: 2 CGCGGCCA. The amplified DNA using primer sequence SEQ ID No: 1 AATGCAGC was placed in lanes 1 and 4 of a gel prepared as above. The amplified DNA using primer sequence SEQ ID No: 2 CGCGGCCA was placed in lanes 2 and 5 of the same gel. A BstN I digest of plasmid pBR322 was placed in lanes 3 and 6 as a reference. The DNA was resolved by electrophoresis (5% polyacryamide-7M urea gel supported by GELBOND PAG polyester backing) as described above. After electrophoresis, the gel was divided into two halves prior to staining. The gels were then treated in accordance with the techniques given in Table I.

TABLE I

| Step | Standard Procedure[a,c] | Present Invention[d] |
| --- | --- | --- |
| Fix | 10% acetic acid; 45 min. | 10% acetic acid; 20 min. |
| Wash | 10% Ethanol; 5 min. | Water; 2 min., 3 times |
| Pretreat | K$_2$Cr$_2$O$_7$ (1 g/l), 0.2 ml HNO$_3$/l; 5 min. | — |
| Rinse | Water; 2 min., 3 times | — |
| Impregnate | AgNO$_3$ (2 g/l); 30 min. | AgNO$_3$ (1 g/l), 1.5 ml 37% HCOH/l; 30 min. |
| Rinse | Water; 20 sec. | — |
| Develop[b] | Na$_2$CO$_3$ (30 g/l), 0.5 ml 37% HCOH/l; 5–10 min. | Na$_2$CO$_3$ (30 g/l), 1.5 ml 37% HCOH/l, Na$_2$S$_2$O$_3$.5H$_2$O (2 mg/l); 2–5 min. |
| Stop[b] | 10% Acetic acid; 5 min. | 10% Acetic Acid, 5 min |

[a]Adapted from C. R. Merril, D. Goldman, S. A. Sedman, and M. H. Ebert, Science, Vol. 211, pp. 1437–1438 (1981).
[b]At 10° C.
[c]Used to stain lanes 4–6.
[d]Used to stain lanes 1–3

Each half of the gel was developed until a faint background was apparent. The gel half stained using the method of the present invention showed black bands on a pale yellow background. The half stained with the standard protocol showed orange-brown bands on a grey background. The stained gels were soaked in 50% ethanol for 10 minutes and then dried at room temperature. The two halves were then reassembled to avoid photographic bias. FIG. 1 shows the result of the staining.

The reduction of silver by formaldehyde is concentration dependent. An increase in the concentration of 37% formaldehyde solution, from 0.5 ml/l to 6.0 ml/l, increases sensitivity but also increases background staining while reducing development time. Optimal band intensity of nucleic acids contained in polyacrylamide gels has been discovered by the present inventors to occur at 1.5 ml/l of 37% formaldehyde with a development time that is approximately one-third the time required by standard techniques (such as C. R. Merril, D. Goldman, S. A. Sedman and M. H. Ebert, *Science,* Vol. 211, pp. 1437–1438 [1981]).

Thiosulfate dissolves insoluble silver salts by complex formation. This removes silver ions from the gel surface and reduces non-specific staining. Image development in the presence of different sodium thiosulfate concentrations (2 mg/l to 64 mg/l) was investigated at varying formaldehyde concentrations. The result was a reduction of background staining with no apparent change in developing time. A concentration of 2 mg/l of sodium thiosulfate (4 µM in thiosulfate) gave a silver stain of superior quality. The presence of thiosulfate further eliminated the formation of a dark precipitate in the gel and developer solution which obviated the need for a rinse after impregnation of the gel.

There are many more bands visible using the method of the present invention. A comparison of lanes 1–3 (using the method of the present invention) with lanes 4–6 (using the standard method) shows that not only are there more bands visualized using the method of the invention but, in addition, those bands are better defined (i.e., sharper). Individual bands are detectable to 1 pg/mm$_2$ band cross-section.

Therefore, the method of the present invention visualizes nucleic acids in polyacrylamide gels to the same sensitivity as radioisotope markers without the risk involved with those markers. In addition, the method of the present invention does not have the complexity of prior art silver staining methods.

Various features of the invention which are believed to be new are set forth in the appended claims.

---

---

What is claimed is:

1. An improved method of visualizing nucleic acid fragments of various lengths on an electrophoresed polyacrylamide gel with more accurate image development and improved sensitivity of detection of the nucleic acids fixed on the washed gel which method comprises without oxidation or reduction pre-treatment of the gel, impregnating the washed and fixed gel with a solution of silver nitrate of a concentration of between about 0.5 g/l and about 1.5 g/l % and aqueous formaldehyde of a concentration of between about 30% and about 45% at a concentration in said solution of about 1.0 m/l and about 2.0 m/l, for between about 20 to 40 minutes, developing the image of the nucleic acids on the impregnated gel containing said nucleic acids with a solution which comprises sodium carbonate, aqueous formaldehyde of a concentration of between about 30% to about 45% and sodium thiosulfate pentahydrate, the concentration of sodium carbonate being between about 20 g/l and about 40 g/l, the concentration of formaldehyde in said solution being between about 1 ml/l and about 2.0 ml/l, the concentration of the thiosulfate pentahydrate of between about 2.0 mg/l and 3.0 mg/l, for a period between about 2 and about 5 minutes, and stopping the development of the image of the nucleic acids by treating the developed gel with acetic acid.

2. The method of claim 1 which comprises washing the impregnated gel before developing the image.

3. The method of claim 1 wherein the developing step is carried out at a temperature in the range of about 8° C. to about 12° C.

4. The method of claim 3 wherein the amount of nucleic acids detectable by visual inspection is about 1 pg/mm$^2$.

5. The method of claim 1 wherein the gel is a back-supported gel.

6. The method of claim 5 which comprises drying the gel and producing a permanent record of the original nucleic acid fragments.

7. The method of claim 1 wherein the formaldehyde concentration is about 37%.

8. The method of claim 1 wherein the gel is treated in the stopping step for between about 3 and 7 minutes with the acetic acid in a concentration in the range from about 5 to about 15%.

9. The method of claim 1 wherein the formaldehyde concentration is 37%.

10. The method of claim 3 wherein the gel is a polyester film backed supported gel.

11. The method of claim 10 which comprises drying the gel and producing a permanent photographic record of the original nucleic acid fragments.

* * * * *